United States Patent [19]

Farone et al.

[11] Patent Number: 5,756,716

[45] Date of Patent: May 26, 1998

[54] SUGAR-ESTER MANUFACTURING PROCESS

[75] Inventors: William A. Farone, Orange County, Calif.; Robert W. Serfass, York, Me.

[73] Assignee: Kimball Chase Tech. Ltd., Portsmouth, N.H.

[21] Appl. No.: 481,647

[22] Filed: Jun. 7, 1995

[51] Int. Cl.$^6$ .................................................. C07H 1/00
[52] U.S. Cl. ...................... 536/120; 536/18.5; 536/115; 536/119; 536/127
[58] Field of Search .................................. 536/115, 119, 536/127, 120, 18.5

[56] References Cited

U.S. PATENT DOCUMENTS

| | | | |
|---|---|---|---|
| 2,812,324 | 11/1957 | Huber et al. | 536/115 |
| 2,893,990 | 7/1959 | Hass et al. | 536/115 |
| 2,903,445 | 9/1959 | Osipow et al. | 536/1.11 |
| 2,970,142 | 1/1961 | Hass | 536/120 |
| 2,997,490 | 8/1961 | Huber | 536/115 |
| 3,054,789 | 9/1962 | D'Amato | 536/115 |
| 3,644,333 | 2/1972 | Osipow et al. | 536/115 |
| 4,683,299 | 7/1987 | Kea et al. | 536/119 |
| 4,710,567 | 12/1987 | Kea et al. | 536/119 |
| 4,983,731 | 1/1991 | Wagner et al. | 536/127 |

FOREIGN PATENT DOCUMENTS

| | | |
|---|---|---|
| 872293 | 8/1956 | United Kingdom . |
| 859305 | 7/1958 | United Kingdom . |

OTHER PUBLICATIONS

Sugar Outlook by K. Jeffrey & Suses of Sucross Monopalmitate in Food Products by N. Ishler 15pg Application of Sucross Esters in Cosmetics by H. Robinette, Jr. 12 pgs.

Fat–Sugar Esters as/Herbicide Adjuvants by H. Watkins 5 pgs.

Effectiveness of Fat–Sugar Derived Surfactants on Absorption of Nutrient Ions Through Leaf Surfaces by D. Cantliffe 5 pgs.

Applications of Sucroglycerides in Foods by H. Passedouet, B. Loiseau, R. Antoine 4 pgs.

Laundering Performance of Tallow Derived Surfactants by C. Rader & A. Schwartz 8 pages., "Sugar Esters Symposium", 1968.

Performance Characteristics of Sucros Ester Detergents by: C. Rader & A. Schwartz 11 pages, 1968, "Sugar Esters Symposium".

Evaluation of sucros Monotallowates in Heavy Duty Detegrents 7 pgs, "Sugar Esters Symposium", 1968.

Applications of Sugar Esters in Foods by T. Kawamata 5 pages, "Sugar Esters Symposium", 1968.

Reflections on Water Pollution Problems by C. Wayman: (7 Pages), Sugar Esters Symposium, 1968.

New Prospects in Animal Feeding: Sucroglycerides; by Passedouet, Loiseau: pp. 46 Through 59, Sugar Esters Symposium, 1968.

Zuckerester: Ester Von Saccharose Mit Speisefettsauren (pp. 142 Through 153 & 205 Through 210, 1985.

Carbohydrates, Chapter 2 pp. 13 Through 42, 1983.

Analytical Chemistry vol. 32, 1960, Determination of Free Fatty Acids in Fat; by I Hornstein, J.A. Alford, L.E. Elliott pp. 540 Through 542.

Sisterna Sucrose Esters of Fatty Acids—A Unique Class of Emulsifiers for/Food Industries 13 pgs, 1994.

The Prep of Alkyl Esters From Fatty Acids & Lipids by W. W. Christie pp. 171–197.

Sucrose Fatty Acid Esters, Methods of Assay test—14 pages, No Date.

Alcoholysis, Saponification and the Preparation of Fatty Acid Methyl Esters by R. L. Glass pp. 919–925.

One–Stage Synthesis of Raffinose Fatty Acid Polyesters C. C. Akoh & B. G. Swanson—Journal of Food Science vol. 52:1570, 1987, 7 pages.

Emulsification Properties of Polyesters & Sucrose Ester Blends II: Alkyl Glycoside Polyesters by C. C. Akoh & C. V. Nwosu Dept of Food Science & Animal Ind., Huntsville, Al. vol. 69, No. 1 (Jan. 1992) pp. 14–19.

Liquid Chromatography and Postcolumn Reaction Modes by R. Weinberger, P. Yarmchuk & L. C. C. Love: Seton Hall Univ.; NJ Analytical Chem., vol. 54, No. 9, Aug. 1982; pp. 1552–1558.

Synthesis & Properties of Alkyl Glycoside & Stachyose Fatty Acid Polyesters; by C. C. Akoh & B. G. Swanson; Dept of Food Science & Human Nutrition, College of Ag & Home Econ Res Ctr; WSU, Wa; JAOCS, vol. 66, No. 9, Sep. 1989, 7 pages.

Surface jActivity of Sucrose Palmitates; by G. S. Fisher, H. J. Zeringue, Jr. & R. O. Feuge; USDA, New Orleans; from The Journal of the Amer. Oil Chemists' Soc'y, vol. 54, No. 2, pp. 59–61 (1977).

(List continued on next page.)

*Primary Examiner*—Elli Peselev
*Attorney, Agent, or Firm*—John J. Connors; Connors & Assoc.

[57] ABSTRACT

Disclosed is a process for manufacturing an sugar ester product of a sugar and a fatty acid. First, a fatty acid and methyl or ethyl alcohol is reacted in the presence of sulfuric acid catalyst to produce a fatty acid ester and water. The sulfuric acid catalyst is neutralized with a metal carbonate to make a metal sulfate, with the fatty acid ester being separated from the metal sulfate, the alcohol and the water. The recovered fatty acid ester is reacted in the presence of a metal carbonate catalyst with sugar dissolved in dimethyl sulfoxide to produce the sugar ester product and alcohol. The dimethyl sulfoxide is separated from the reaction mixture by vacuum distillation, and then water is added to emulsify the sugar ester product and unreacted fatty acid ester. The unreacted sugar and the metal carbonate is dissolved in the water. Next, the emulsified sugar ester product and unreacted fatty acid ester is separated from the water containing dissolved unreacted sugar and metal carbonate by breaking the emulsion of the sugar ester product and unreacted fatty acid ester. The sugar ester product is purified by dissolving the unreacted fatty acid ester in ethyl acetate, and substantially all the dimethyl sulfoxide, alcohol, and ethyl acetate is recovered for reuse in the process. Finally, substantially all the unreacted sugar in a concentrated useful form is recovered.

27 Claims, 7 Drawing Sheets

OTHER PUBLICATIONS

Purification of Sucrose Esters by Ultrafiltration; H. J. Zeringue, Jr. & R. O. Feuge; from; The Journal of the Amer. Oil Chemists Soc'y., vol. 53, No. 12, pp. 719–721 (1976).

Properties of the Fatty Acid Esters of Amylose by A. T. Gros & R. O. Feuge; from: The Journal of the Amer. Oil Chem Soc'y. Jan. 1962 Issue, vol. 39, No. 1.; p. 10.24.

Chemical Abstracts; vol. 75, 1971 ; 4 pgs.

Emulsification Properties of Polyesters and Sucrose Ester Blends I: Carbohydrate Fatty Acid Polyesters; C. C. Akoh; Dept of Food Science & Animal Ind., A&M University. JAOCS, vol. 69, No. 1 (Jan. 1992).

Sugar Esters Patent Search for 1992 and 1993 to date. Derwent's World Patent Database. File 351:Derwent World Patents Index–Latest 1981+; DW=9338, UA=9334, UM=9317.

Food & Drug Admin., HHS; CFRCh. 1 (Apr. 1, 1992 Edition) pp. 85–87.

Present Status of Porcesses for Production of Esters by H. Iwatsuki, Mgr. of research, Dai Nippon Seito Kaisha, Ltd. 5 Pgs.

Nebraska–Snell Process/by M. Kammerlohr, Asst Att'y Gen, State of Neb. 4 Pgs.

Early History of Suvcrose Esters; by H. B. Hass, Consult, M. W. Kellogg Co. 4 Pgs.

Ryoto Sugar Ester Ttech Info.; Mitsubishi–Kasei Food Corp (MFC) pp. 1–22, Jan. 1991.

SUGAR-ESTER MANUFACTURING PROCESS

BACKGROUND OF THE INVENTION

1. Field of the Invention

This invention relates to a process for making sugar esters where substantially all unreacted ingredients are recovered as valuable products or reused in the process, thereby eliminating discharging pollutants into the environment.

2. Background Discussion

In the late 1950s and early 1960s interest developed in "natural" alternatives to surface active agents, also known as surfactants, used in detergent formulations, drugs, cosmetics, toiletries and foods. The soaps (sodium and potassium salts of fatty acids) were replaced by the petroleum derived surfactants slightly before this time. Nevertheless, there was continued interest in using the fatty acids derived from beef tallow and vegetable oils in better surfactants. One class of surfactants that aroused great interest was the esters of sugars and fatty acids.

While there has been much work done to find various methods for synthesizing and purifying sucrose esters, there are only a few commercial source of these materials that meet the Food and Drug Administration requirements, one being Ryoto Sugar Esters made by the Mitsubishi-Kasai Food Company. The history of the sucrose esters, and their specifications, are discussed in the Ryoto Sugar Ester Technical Information Bulletin and refer back to the work originally sponsored by the Sugar Research Foundation in 1954.

When sucrose and fatty acid are reacted to form the ester there are eight positions on the sucrose molecule where the ester can form. Typically, monoesters, diesters and triesters are formed with a small amount of higher esters. When the reaction is with a single fatty acid, for example, stearic acid or lauric acid, thin layer chromatographic analysis and liquid chromatographic analysis shows that there are many different esters that form, typically 2–4 monoesters and up to 6–8 diesters. If a mixture of acids is used, such as when a commercial fatty acid mixture is used, the number of isomers is even higher. Each of the fractions have slightly different properties. For example, the lauric acid esters are liquid at room temperature while the stearic acid esters are solid. Other products and mixtures make products that are semi-solids. They have differing solubilities in water and organic solvents, but for the most part, as with most surfactants, the longer chain length esters, for example, sucrose stearates, are very insoluble in water and low chain alcohols. Although desirable, these differing solubilities and physical properties make an integrated production facility a difficult goal.

In order for a sucrose ester manufacturing process to be commercially useful it must be able to produce esters which meet the following FDA requirements:

(a) at least 80% by weight mono-, di- and tri-esters,
(b) less than 5% by weight free sucrose,
(c) has an acid value is less than 6,
(d) no more than 2% by weight ash,
(e) no more than 350 parts per million ethyl acetate,
(f) no more than 3 parts per million arsenic,
(g) no more than 50 parts per million heavy metals,
(h) no more than 10 parts per million lead,
(i) no more than 10 parts per million methyl ethyl ketone,
(j) no more than 10 parts per million methyl alcohol,
(k) no more than 2 parts per million dimethyl sulfoxide,
(l) no more than 10 parts per million isobutyl alcohol.

Although it is not stated specifically in the FDA requirements, the above requirements allow for a significant amount of starting products to be carried over into the final product. For example, almost all of the previous techniques recommend the use of the methyl esters of the fatty acids to make the final sucrose ester by transesterification. This leaves behind methyl esters in significant quantities, for example, 0.25% by weight residual methyl ester means that methanol will be generated by ingestion of the methyl ester by hydrolysis in the stomach that exceeds the FDA standard of 10 parts per million. The literature does not teach a commercial process to meet all of the FDA requirements.

The classic method for the production of the sucrose esters is best illustrated by the production of sucrose stearate. It is, however, much more difficult to produce other chain lengths. This fact has not been discussed in the prior art. It almost appears that the sucrose stearate was studied and then it was assumed that the methods would apply to sucrose laurate, which is also referred to as sucrose cocoate after the coconut oil source of the lower chain length fatty acids.

In the early processes dimethyl formamide (DMF) was used as the solvent. The methyl ester of the fatty acid was made and this methyl ester was reacted with sucrose in the DMF in the presence of a catalyst such as potassium carbonate for 4–6 hours at 83°–95° C. Typical recipes (all are parts by weight) used 30 to 127 parts sucrose to 30 parts methyl stearate, 2 parts potassium carbonate and 300 parts solvent. These methods achieved high yields of 60–75% by weight. The basic problem was purifying the reaction mixture. The reaction products are highly viscous containing partially decomposed sugars and solvents.

This lead to a series of attempted improvements. For example, U.S. Pat. No. 3,644,333 to Osipow et al based on U.S. Pat. No. 3,480,616, tried to eliminate the use of a solvent by making a "transparent emulsion." Typically, in this process, sucrose was mixed with methyl stearate and sodium stearate and a significant amount of previously prepared sucrose ester. Potassium carbonate was still used as the catalyst, but water was used as the solvent. The water was driven off and then the reaction was completed using the mixture as its own solvent. Although much was made in the patent and the literature about the requirement for the emulsion, it should be noted that Example V in U.S. Pat. No. 3,644,333 does not make the emulsion and the inventors indicate they achieve the same yield of products. The yields are very low, on the order of 30–35% by weight. Further, there was much more waste and degraded products and the desired product was much more difficult to remove from the reaction mixture. A typical recipe used 80.4 parts sucrose, 75 parts methyl stearate, 12.3 parts sodium stearate, 40.5 parts sucrose monostearate, 0.75 parts potassium carbonate, and 166.8 parts water. In addition to the low yields, it was been found that the inclusion of sodium stearate, or significant quantities of any alkali fatty acid salt, results in a product which is much more difficult to purify and, in particular, gives a product which does not meet the 2% maximum ash FDA requirement.

Alternative methods have been described by Feuge. For example, in U.S. Pat. No. 3,714,144, he uses the sodium, potassium or lithium soap of the fatty acid in a molten sugar solution. The reaction proceeds for 2–20 minutes under vacuum at 170°–190° C. The product is made in very low yield and the destroyed sugar and alkali metals are very difficult to remove. As with the Osipow process, the quality of the product is poor compared to the commercially accepted solvent techniques.

To help with the production of the esters, several relatively complicated schemes have been devised to purify the reaction mixtures. For example, Kea et al in U.S. Pat. No. 4,710,567 teach the use of the addition of an aqueous salt solution to help purify the ester followed by a three phase separation. Not only are three phase separations very costly to perform commercially, but the resultant salt streams are very difficult to reuse and the waste from the process is enormous.

Wagner et al in U.S. Pat. No. 4,983,731 teach a particular method of purifying the sucrose ester from a solvent free production process by dissolving the ester in a lower aliphatic (C1–C4) alcohol to form a solution over an undissolved residue. They claim that the residue is removed and then the desired product precipitated from the alcohol solution with water. In practice it is found that the desired products are only very sparingly soluble in ethanol, the desired alcohol from a food use point of view. Thus, tremendous amounts of ethanol are needed. Furthermore, the yields are extremely low and the product is not acceptable. For example, in their Example 1 they end up with a product that is 16% fatty acid, and in Example 2 the product has 22% fatty acid when the FDA allowable amount is 3%.

SUMMARY OF THE INVENTION

It is the objective of this invention to provide a commercial process that overcomes the limitations of previous processes, with particular attention to providing a integrated production facility that has no liquid waste streams and minimal air emissions. This is not a trivial point, since the processes which are more economically viable have always been plagued by high waste streams of many solvents. Specifically, the objective of the present invention is to:

1. Produce sugar esters from various feedstock fatty acids in high yield and purity in a single integrated process facility.
2. Recycle, reuse or sell as by-products all output streams in the process.
3. Reduce the number of handling steps and develop a product to FDA specifications with less effort, cost and equipment.
4. Provide a process with integrated quality control such that the processing of the product can be tracked at each step of the process.

The sugar ester manufacturing process of this invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENT," one will understand how the features of this invention provide its benefits, which include providing a high yield of sugar ester that meets FDA requirements with essentially no discharge of pollutants into the environment.

The process of this invention for manufacturing an ester product of a sugar and a fatty acid includes several steps which utilize the features of this invention:

Step 1

The first step is to react a fatty acid and methyl or ethyl alcohol in the presence of sulfuric acid catalyst to produce a fatty acid ester and water. Excess alcohol is used to drive the reaction essentially to completion. The reaction mixture of this step 1 is monitored to detect completion of the reaction when no more than 1 percent by weight of the fatty acid remains in the reaction mixture. The fatty acid is derived from natural oils and fats. Suitable acids are hexanoic, octanoic, decanoic, lauric, myristic, myristoletic, palmitic, stearic, oleic, ricinoleic, linoleic, linolenic, arachidic, eicosenoic, behenic, and erucic fatty acids.

Step 2

After step 1, the second step is to neutralize the sulfuric acid catalyst with a metal carbonate to make a metal sulfate, and separating by filtration the metal sulfate from the fatty acid ester, the alcohol and the water. Potassium carbonate is preferred, but sodium, magnesium, or calcium carbonate may also be used. The metal sulfate is recovered as a by-product which may be sold. The alcohol and water are separated from the fatty acid ester and reused in the process.

Step 3

In step 3, the fatty acid ester from step 2 is reacted in the presence of a metal carbonate catalyst, again preferably potassium carbonate, with sugar dissolved in dimethyl sulfoxide to produce the sugar ester product and alcohol. The reaction is the well known transesterification process. The reaction mixture in this step 3 is monitored to detect completion of the reaction when no more than 15 percent by weight of the fatty ester remains in the reaction mixture. In most cases, no more than 5 percent by weight of the fatty ester remains in the reaction mixture. Upon completion of the reaction of step 3, the metal carbonate catalyst is neutralized with sulfuric acid to make a metal sulfate. Preferably, excess sugar is used in step 3 in order to favor the production of monoester product. The sugar is selected from the group consisting of sucrose, glucose, fructose, xylose, arabinose, lactose, melibiose, galactose, mannose, raffinose and cellobiose. When the reaction time and temperature in step 3 is preferably increased as the chain length of the fatty acid decreases. The reaction time is from 3 to 6 hours and the reaction temperature is from 90 to 105 degrees Celcius when the average carbon chain length of the fatty acid is 16 or greater, and the reaction time is from 8 to 24 hours and the reaction temperature is from 105 to 125 degrees Celcius when the average carbon chain length of the fatty acid is less than 16. The dimethyl sulfoxide is refluxed during this step 3 at a temperature above the boiling point of the alcohol being produced during the transesterification reaction and from step 1 to remove the alcohol. The metal carbonate is identical in both steps 1 and 3.

Step 4

In step 4, the dimethyl sulfoxide is separated from the reaction mixture by vacuum distillation. After dimethyl sulfoxide is removed, water is then added to the reaction mixture. The sugar ester product and unreacted fatty acid ester are emulsified and the unreacted sugar and the metal carbonate are dissolved in the water. The dimethyl sulfoxide separated in this step 4 is reused in the process.

Step 5

The emulsified ester product and unreacted fatty acid ester are separated from the water containing dissolved unreacted sugar and metal carbonate. This separation is achieved by breaking the emulsion of the ester product and unreacted fatty acid ester. This is accomplished by two different methods depending on the chain length of the fatty acid.

For lower chain sugar ester where the average carbon chain length of the fatty acid is less than 16, the sugar ester product and unreacted fatty acid ester are dissolved in a solvent which is immiscible with the water. This forms two separate liquid phases, one phase including the solvent, the ester product and unreacted fatty acid ester, and the other phase including the water, the unreacted sugar and the metal carbonate. The preferred solvent is n-butanol to form an n-butanol phase and a water phase. Then the two phases are physically separated, for example, by filtration, decanting or centrifuging. For fatty acid having an average carbon chain length of less than 16, the sugar ester product and the unreacted fatty acid ester are recovered by vacuum distillation of the solvent, for example, the n-butanol. Other suitable solvents depending on the sugar ester product being made include t-butyl alcohol, 2-butanol, hexane, heptane, methyl isobutyl ketone, and isomers of amyl alcohol.

For higher chain sugar ester where the average carbon chain length of the fatty acid is 16 or greater, adding ethyl alcohol or methyl ethyl ketone to the emulsion to break the emulsion of the ester product and unreacted fatty acid ester.

The metal carbonate in the water phase is recovered when unreacted sugar is recovered as molasses. It serves as a mineral supplement to the molasses when used as animal feed.

Step 6

In this step 6, the ester product from step 5 is purified by dissolving the unreacted fatty acid ester in a suitable solvent, preferably in ethyl acetate. The ester product and the unreacted fatty acid ester remain together as a mixture after the separation of step 5. This mixture is washed with the ethyl acetate which dissolves the unreacted fatty acid ester. When no more than 5 percent by weight of the unreacted fatty acid ester remains in the sugar ester product, washing is discontinued. Most of the time, less than 1 percent by weight of the unreacted fatty acid ester remains in the sugar ester product after washing. When the average carbon chain length of the fatty acid is 16 or greater, the mixture of the sugar ester product and the unreacted fatty acid ester is washed with dry ethyl alcohol to remove any trace water in the mixture prior to washing with the solvent for the unreacted fatty acid ester. When ethyl acetate solvent is used, the sugar ester product is completely purified by removal of traces of ethyl acetate so that no more than 350 part per million of ethyl acetate remain in the final ester product.

Step 7

In step 7, substantially all the dimethyl sulfoxide, alcohol, and ethyl acetate is recovered for reuse in the process by fractional distillation and drying of the non-aqueous solvents.

Step 8

Finally, substantially all the unreacted sugar in a concentrated useful form is recovered.

Steps 1, 2 and 3 are by batch and the other steps are either batch or continuous. In this process, all liquid, solid, and solution streams from the process are reused or recovered as useful by-products. As required, an on-line methods of monitoring and controlling process are employed, preferably using FT-IR methods described in U.S. Pat. No. 5,262,961. Where the sugar used is sucrose, the sugar ester product meets FDA standards.

DESCRIPTION OF THE DRAWING

The preferred embodiment of this invention, illustrating all its features, will now be discussed in detail. This embodiment depicts the novel and non-obvious process of this invention making, for example, sucrose stearate as shown in the accompanying drawing, which is for illustrative purposes only. This drawing includes the following figures (Figures), with like numerals indicating like parts.

DETAILED DESCRIPTION OF THE PREFERRED EMBODIMENT

Figure 1:
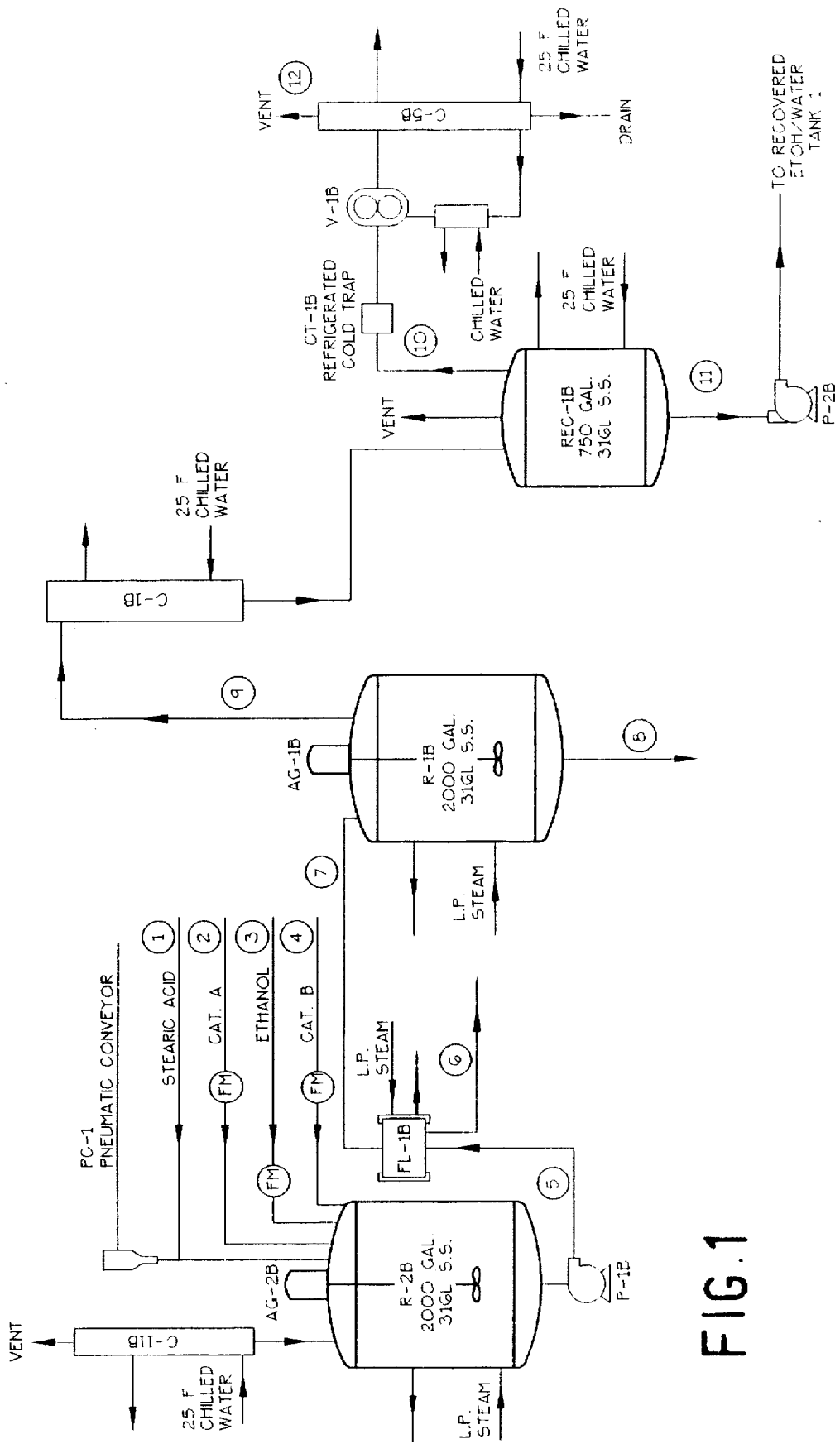
FIG. 1 is a process flow diagram showing the way the ethyl stearate is manufactured from stearic acid and ethanol.

The process of this invention, which is best explained in terms of eight steps, has been tested in a pilot plant with a 50 gallon reactor and sufficiently large batches made to understand the details of the process as described.

In Step 1, the ethyl or methyl ester is made. We prefer the ethyl ester since traces left in the product will not produce methanol when ingested. An important part of the process is the degree of completion of this reaction. Sulfuric acid is used as the catalyst with plenty of excess ethanol to insure reaction completion. This portion of the process is monitored by Fourier Transform Infrared Spectroscopy, or similar fast reliable method (herein FT-IR methods), to insure that there is very little free fatty acid left, typically less than 0.5%.

U.S. Pat. No. 5,262,961, entitled Method For Monitoring and Controlling A Chemical Process describe a preferred way to monitor the various streams utilized in the present invention. According to this method, samples of a stream are analyzed on-line in real time, with the results being used essentially immediately to make adjustments in process conditions to achieve optimal results, for example, highest yields. This method of monitoring and controlling the process of the present invention comprises (a) measuring the concentration of process components in samples from the process using a spectrometric instrument to obtain spectral data characteristic of the process components, (b) analyzing the spectral data using a chi-squared mathematical technique to determine the unknown concentration of process components in said samples, and (c) monitoring the physical parameters of the process and altering said physical parameters based on the determination of concentration of process components in step (b) as required to optimize the process.

In Step 2, the acid in Step 1 is neutralized with potassium carbonate. This makes potassium sulfate, but it should be noted that potassium carbonate will be also used in the next step as the catalyst and no problems occur if too much potassium carbonate is added. Thus, we limit the chemicals and the by-products. The potassium sulfate is separated for the fatty acid ester by filtration or centrifugation. Any ethanol associated with it in the cake is recovered. The recovered potassium sulfate is a useful soil amendment by-product. Next the ethanol is separated from the fatty acid by vacuum distillation, leaving the desired ethyl stearate. Note, that some water was produced in the esterification which goes off with the ethanol. The ethanol is dried using molecular sieves periodically to keep it nearly anhydrous.

In Step 3, the ethyl stearate is dissolved in dimethyl sulfoxide (DMSO) in a reaction vessel adding sugar and potassium carbonate. The sugar is usually in excess to produce preferentially monoesters. Using this technique, the reaction time varies with the chain length. When making the sucrose stearates, the reaction time can be as little as 3 hours, with 4 hours preferred, and 6 giving more of the di- and tri-esters. As the chain length of the acids decrease, the reaction time increases until about 20 hours is required at a slightly higher temperature (125° C.) for lauric acid, for example, the coconut fatty acids of high C12 purity. The DMSO solvent is safer than DMF and allowed by FDA. It is also useful to reduce degradation to "reflux" the DMSO slightly. This is accomplished by drawing a partial vacuum on the DMSO, just enough to cause it to continually recondense in a condensing column placed just above the reactor. It should be noted that this also has the effect of removing any ethanol that was left in the ethyl esters used in the reaction or removing the ethanol that comes off in the transesterification. This ethanol comes off since the reaction is being run above the boiling point of ethanol. The ethanol is collected for reuse.

In Step 4, after the reaction is complete as identified by analysis of the reaction mixture (again FT-IR methods are convenient), the DMSO is distilled off simply by increasing the vacuum. The potassium carbonate may be left "as is" or, optionally, neutralized with sulfuric acid (again making potassium sulfate) before the distillation. The neutralization is useful with some fatty acid products that may degrade during DMSO removal. Water is added to the reaction vessel to dissolve the sugar and the potassium sulfate, leaving the sugar ester product suspended in the water as an emulsion. The product is not soluble in water to any significant extent, but it forms an emulsion which is very difficult to separate from the water.

Step 5 takes two forms depending on the chain length of the acid used. The lower chain length esters (less than C16) are soluble in n-butanol, and n-butanol is only slightly soluble in water. By adding n-butanol, the desired sugar ester product, along with any unreacted ethyl ester, dissolve in the n-butanol. The sugar and the potassium sulfate remain in the water. This provides two solutions, in only two phases, which can be separated in a centrifuge. The n-butanol phase is distilled, with the n-butanol being evaporated and the sugar ester product and unreacted ethyl ester recovered as a very soft solid. For chain lengths above C16, the sugar ester product and unreacted ethyl ester have not dissolved in the water. They can be separated by adding a small amount of ethanol or methyl ethyl ketone (MEK) in order to "break the emulsion". This allows separation in a solid bowl centrifuge, a filter, or a decanter.

In Step 6 the unreacted sugar is recovered. In the case of the lower chain length products, the liquid stream is centrifuged, decantered, or filtered, recovering the ethanol (or MEK) for reuse along with the water. The solids that remain after the liquid recovery are sold as an animal feed product, since it is unreacted and caramelized sugar with a small amount of minerals (potassium sulfate or potassium carbonate) and a small amount of sugar ester that may dissolve in the water phase. After the centrifuge in the case of the longer chain length product, or the removal of butanol in the case of the shorter chain length products, there remains a mixture of the desired sugar ester product and unreacted ethyl esters of the fatty acid.

In Step 7, the soft solid or liquid, depending on chain length, is washed with ethyl acetate which removes the ethyl esters. An important preferred method in the case of the longer chain length products, is to wash the cake with dry ethanol to remove water from the cake before washing the sugar ester product with the ethyl acetate. This makes the ethyl acetate wash more efficient. After repeated centrifuge or filtration steps, the liquid stream of ethyl acetate with the unreacted ethyl esters is distilled and the ethyl acetate recovered by vacuum evaporation, leaving the unreacted ethyl esters of the fatty acids which are reused. A high purity sugar ester product remains with less than 2 weight percent unreacted ethyl esters remaining in the final product. All of the purification steps can be monitored with FT-IR methods. Any trace impurity products have very distinctive spectra compared to the final product so one can quickly determine the relative purity that has been achieved.

In step 8 the product can either be dried to remove the ethyl acetate to a final acceptable product (i.e. no more than 350 ppm ethyl acetate remaining) or a final wash can be made with water and ethanol (to break the emulsion). Note, all of the solvents are recovered and the process is very easy to implement on a commercial scale, as illustrated in FIGS. 1 through 7.

The following as an example of making sucrose stearate according to the present invention. Other sugar esters as discussed above may also be made using the process of this invention.

EXAMPLE

Forty (40) pounds of stearic acid was added to 13.75 gallons (90.4 pounds) of ethanol. Two and four tenths (2.4) pounds of 98% sulfuric acid was added and the reaction run by refluxing ethanol at 77° C. until there was less than 0.5% free fatty acid as determined by FT-IR methods. At this point 3.31 pounds of potassium carbonate was added and 1.05 pounds of carbon dioxide is produced. The remaining mass of 135.05 pounds is sent through a filter where 7.9 pounds is removed, including 4.2 pounds of potassium sulfate with 3.76 pounds of ethanol containing a very small amount of water. The potassium sulfate and the ethanol are recovered. The remaining mass of 127.1 pounds is sent to a vessel where the ethanol is removed by vacuum evaporation. Approximately 12 gallons (81.7 pounds) of ethanol is recovered and 45.4 pounds of material containing 43.6 pounds of ethyl stearate is sent to the esterification reaction. The esterification vessel is charged with 32.3 gallons (294.6 pounds) of DMSO. The ethyl ester product is added, 45.4 pounds containing 43.6 pounds of ethyl stearate and 1.6 pounds of ethanol. Ninety five and six tenths (95.6) pounds of sucrose is added along with 2.9 pounds of potassium carbonate. The reaction is run at 95° C. for about 4 hours until samples withdrawn from the reaction vessel indicate substantial reaction completion. Typically 55.3 pounds of sucrose stearate would be formed in four hours. During the reaction a little more than 1 gallon of ethanol (6.75 pounds) is recovered as condensate from a reflux condenser overhead. After completion of the transesterification reaction to produce the sucrose ester, 431.8 pounds of a mixture (approximately 44 gallons) is subject to DMSO removal, with 288.7 pounds of DMSO being recovered. From the previous esterification reaction and DMSO recovery steps, 143.1 pounds of product plus unreacted materials is washed with 286.2 pounds (34 gal) of water. Ethanol (7 gallons, 42.9 pounds) is added to break the emulsion. The mixture is centrifuged, the solids from the centrifuge are washed with an additional 13 gallons of ethanol and the mixture is centrifuged again. From this ethanol "drying" step, 126.8 pounds of material (which was 49.7 pounds of desired product, 61.7 pounds of ethanol and 8.7 pounds of ethyl stearate) is recovered. This 126.8 pounds of material was washed with 17 gallons (126.8 pounds) of ethyl stearate. The total mixture is again centrifuged and 124.2 pounds of "solids" is obtained along with 129.4 pounds of solution from which the ethyl acetate and ethanol may be recovered. The ethyl acetate solution contains 8.3 pounds of ethyl stearate. The solids containing the desired product is sent to the dryer. The 124.2 pounds of solids from the centrifuge after the ethyl acetate wash is dried. Sucrose stearate is recovered as 48.7 pounds of material of which 44.8 pounds is pure sucrose stearate. This is approximately 92% by weight purity, which is well above the 80% by weight purity commercial requirement. About 11 gallons (75.4 pounds) of condensate is obtained for recycling.

INTEGRATED COMMERCIAL FACILITY

FIGS. 1 through 7 depicted an integrated commercial facility for manufacturing sucrose steartate designed to make 800 tons of product per year. The esters of sucrose and fatty acids, in particular the sucrose stearate, are the most popular commercial sugar ester products. Consequently, the process of this invention is illustrated making the sucrose steartate product. It is also possible, however, to substitute other sugars such as, for example, glucose, xylose, arabinose and lactose and achieve similar classes of ester products.

FIG. 1 shows the details of the esterification reaction described in Step 1 above. The stearic acid stream 1, the sulfuric acid catalyst stream 2, the ethanol stream 3, and the potassium carbonate stream 4 are added as required to the reactor R-2B, where the esterification reaction takes place. The stearic acid stream 1 is fed via a pneumatic conveyor (not shown). The reaction is carried out at the boiling point of ethanol. After the reaction is complete, the potassium carbonate stream 4 is added to neutralize the mixture. A small amount of carbon dioxide forms. A chilled condenser C-11B is used to minimize emissions, but some steam and carbon dioxide gas are vented to the atmosphere at acceptable levels with virtually no volatile organic constituents in the vented gas. The mixture is pumped by a pump P-1B through a filter FL-1B to remove the potassium sulfate which leaves as stream 6. The solution proceeds as steam 7 to a reactor R-1B where the ethanol is vacuum evaporated via condenser C-1B into a vessel REC-1B. The recovered ethanol is recycled via stream 11 while a cold trap CT-1B and a vacuum pump V-1B for a distillation system C-5B is set up to minimize losses out the vent stream 12 and return condensate that passes the cold trap CT-1B and condenser C-5B through the drain back to stream 11. The cold trap condensate can also be returned. In this manner virtually all of the ethanol can be reused and volatile organic vapors emissions minimized.

Figure 2:
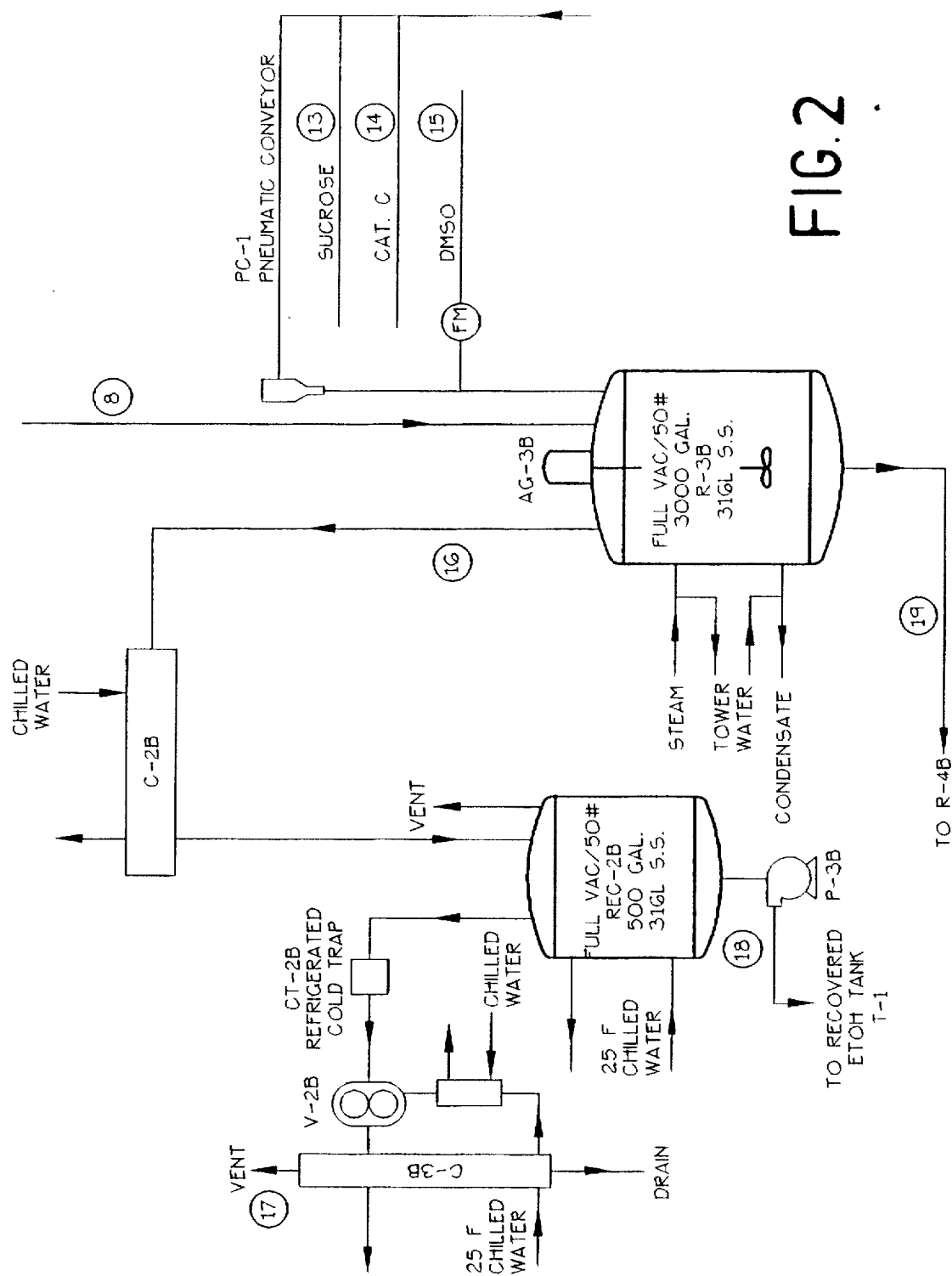
FIG. 2 is a process flow diagram showing the way the sucrose stearate product is made by the transesterification of sucrose and the ethyl stearate.

FIG. 2 shows the esterification reaction. The solvent, DMSO, enters as stream 15, the ethyl stearate enters from the ethyl ester reaction via stream 8. A pneumatic conveyor PC-1 forwards to the reactor R-3B the sucrose and the potassium carbonate catalyst as steams 13 and 14, respectively. During the reaction, reflux 16 is contained by condenser C-2B and vacuum pump V-2B is adjusted to maintain the desired temperature and reflux in the reactor R-3B. The small amount of ethanol that entered the reaction plus the ethanol produced during the reaction is recovered via reflux stream 16 and collected in a recovery vessel REC-2B. The pump P-3B forwards recovered ethanol to the ethanol tank T-1 (FIG. 6) via stream 18. Losses to atmosphere via stream 17 are again negligible due to cold trap CT-2B and in condenser C-3B. After the reaction, the mixture containing the sugar ester product is discharged via stream 19.

Figure 3:
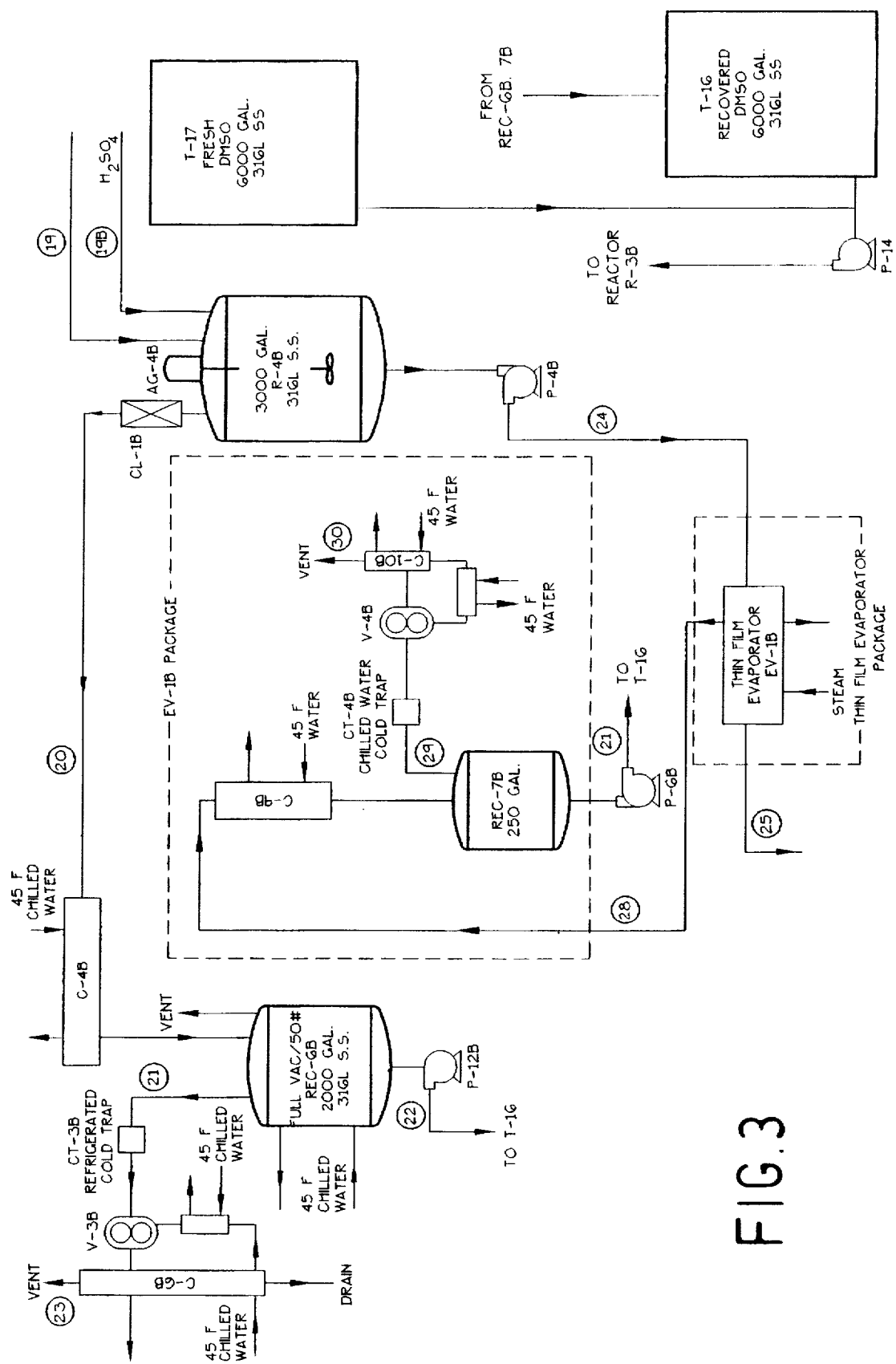
FIG. 3 is a process flow diagram showing the way dimethyl sulfoxide is recovered for reuse in the process.

As shown in FIG. 3, the stream 19 including the sucrose ester product, the solvent DMSO, the metal carbonate catalyst and unreacted reagents are sent to a tank R-4B for recovery of the DMSO. It is optional to also add a small amount of sulfuric acid at this time via stream 19B to convert the potassium carbonate to potassium sulfate. The inorganic material will be recovered later in water solution and it can be recovered either as the carbonate or the sulfate. The DMSO is removed in a two stage process. In the first stage, a vacuum pump V-3B is used to vacuum evaporate the DMSO via stream 20. Again, discharges to the atmosphere via stream 23 are minimized via a collection of vapors in cold trap CT-3B and in condenser C-6B. Approximately 85% by weight of the DMSO is removed in this stage. A molten sugar ester product steam 24 is pumped by pump P-4B through thin film evaporator EV-1B to remove virtually all of the remaining DMSO which is drawn off via stream 28 by a vacuum pump V-4B. Another cold trap CT-4B and condenser C-IOB combination is used to assure maximum recovery and minimum emissions. DMSO streams 22 and 21 from both stages of the DMSO recovery are sent to tank T-16 which holds the recovered DMSO. The sugar ester product, still with unreacted materials and the potassium carbonate is sent to the next stage via stream 25.

Figure 4:
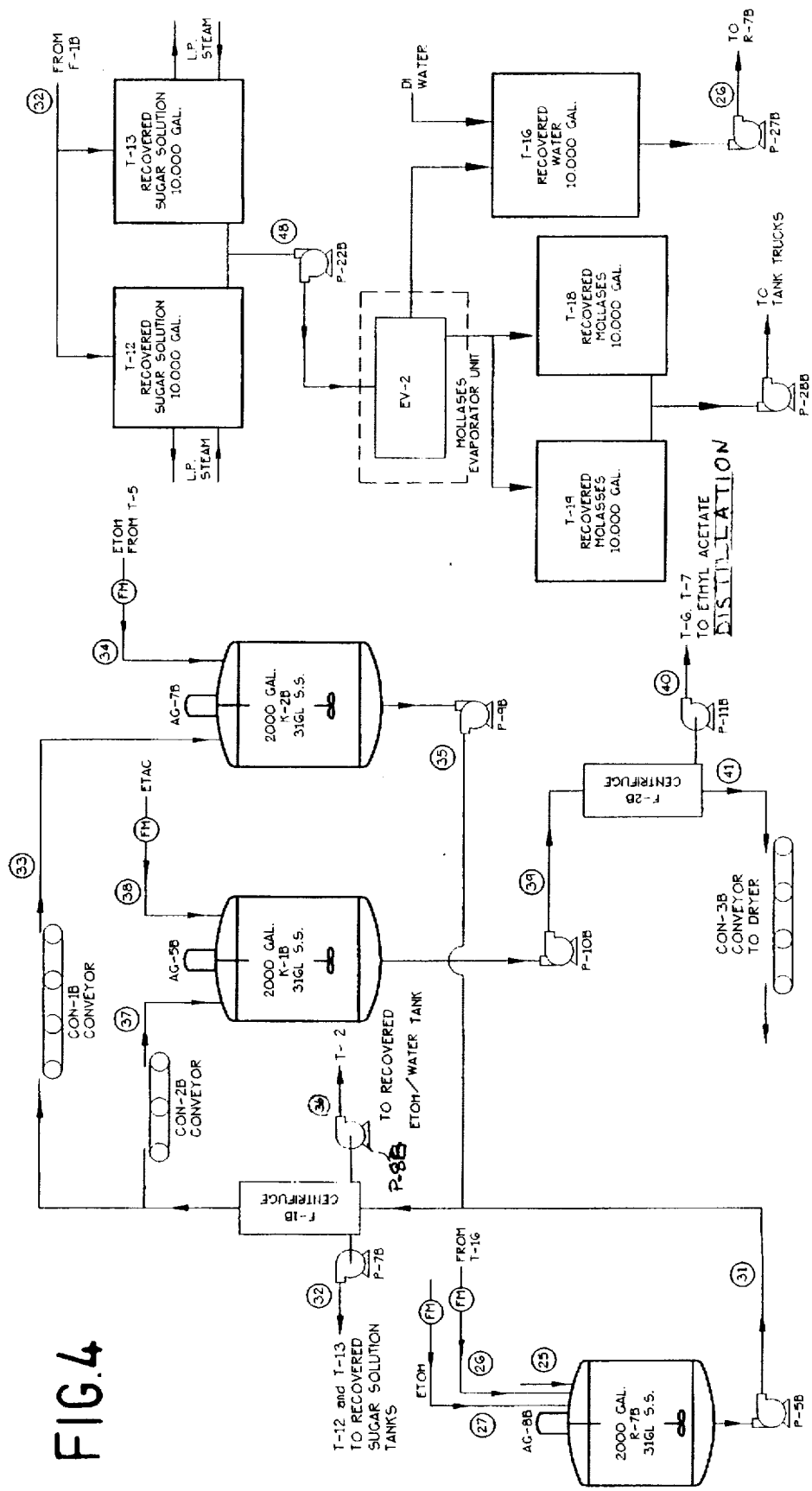
FIG. 4 is a process flow diagram showing the way the sucrose stearate product is purified.

As shown in FIG. 4, the sugar ester product and unreacted ingredients are sent to vessel R-7B. Water is added via stream 26 and a small amount of ethanol is added to break the emulsion which forms due to the presence of the product. The sugar and inorganic salts dissolve in the liquid, leaving a residue which is the desired product and unreacted ethyl stearate. The mixture is sent via stream 31 to centrifuge F-IB where the solids stream 33 is sent by enclosed conveyor CON-1B to container K-2B. The liquids steam 32 is sent to tanks T-12 and T-13 for recovery. Not shown is an evaporator for recovery of the sugar (or molasses) solids in steam 32. The ethanol fraction of the liquids is recovered and sent to tank T-2 (FIG. 6) while recovered water is sent to a water recycle tank T-16. The molasses stream 48 is concentrated up to 40–50% sugar for sale. The sucrose stearate product and ethyl stearate in tank K-2B is "dried" by addition of ethanol via steam 34. The slurry is sent back to centrifuge F-1B via stream 35 and the recovered ethanol is sent via steam 36 to tank T-2. The solid product stream 37 is sent to the ethyl acetate wash tank K-1B via enclosed conveyor CON-2B. Ethyl acetate is added via stream 38 to dissolve the ethyl stearate and the mixture sent via stream 39 to centrifuge F-2B where the ethyl acetate containing the ethyl stearate is sent to tanks T-6 and T-7 via stream 40 and the desired product stream 41 is sent via enclosed conveyor CON-3B to a dryer DR-1B (FIG. 5).

Figure 5:
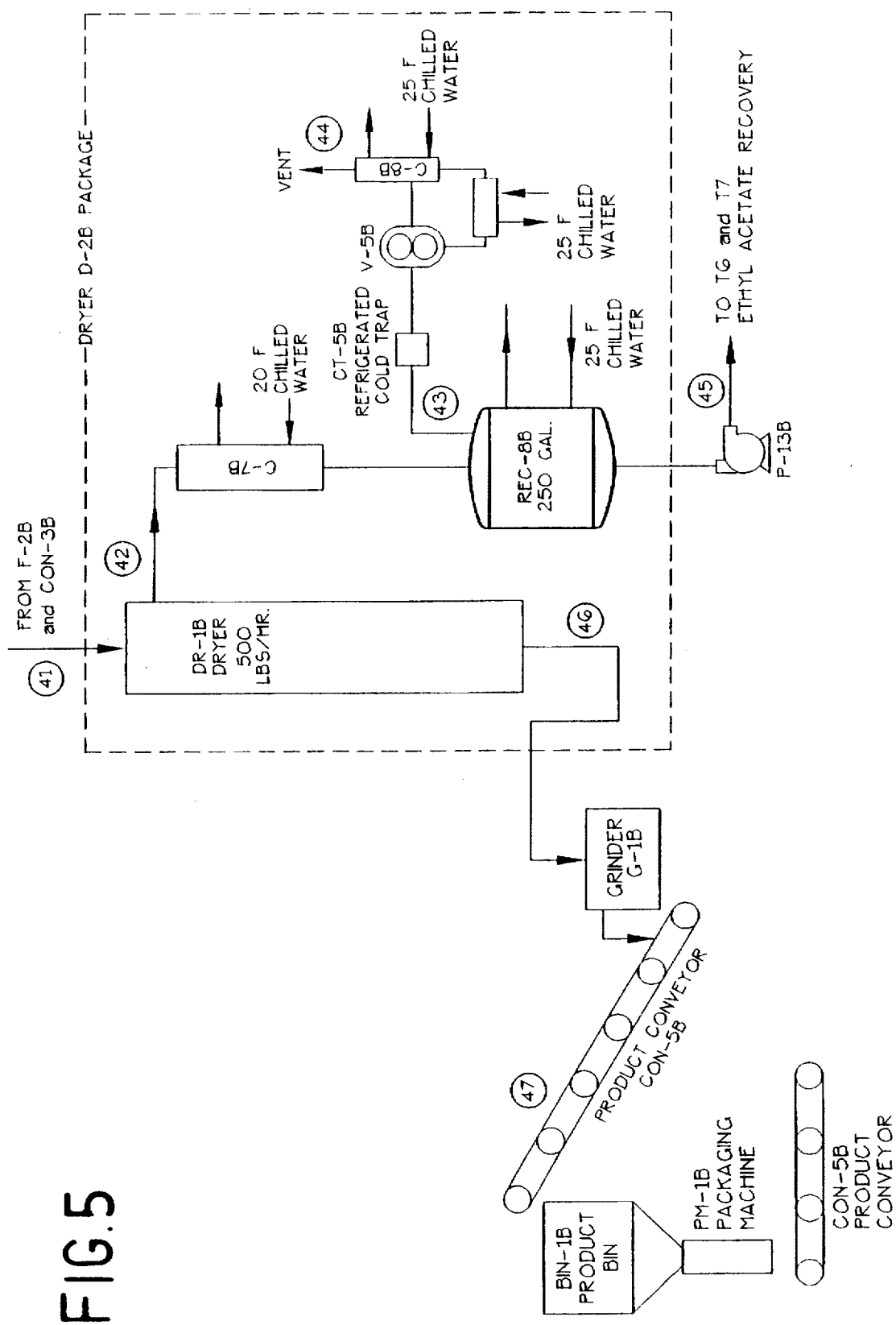
FIG. 5 is a process flow diagram showing the way the sucrose stearate product is dried.

As depicted in FIG. 5, the material from the centrifuge after the ethyl acetate wash enters the dryer DR-1B via stream 41. This vacuum dryer DR-IB removes the ethyl acetate and remaining ethanol via stream 42 using heat and vacuum. The ethyl acetate is condensed in condenser C-7B and enters receiver REC-8B from which it is returned to ethyl acetate recovery tanks T-6 and T-7 via the pump P-13B. The dried product stream 46 enters a grinder G-IB after which it proceeds via product conveyer CON-5B to the packaging equipment. The vacuum pump V-5B, which drives this part of the system, is also protected by a cold trap CT-5B and is followed by another condenser C-8B to maximize recovery and minimize air emissions.

Figure 6:
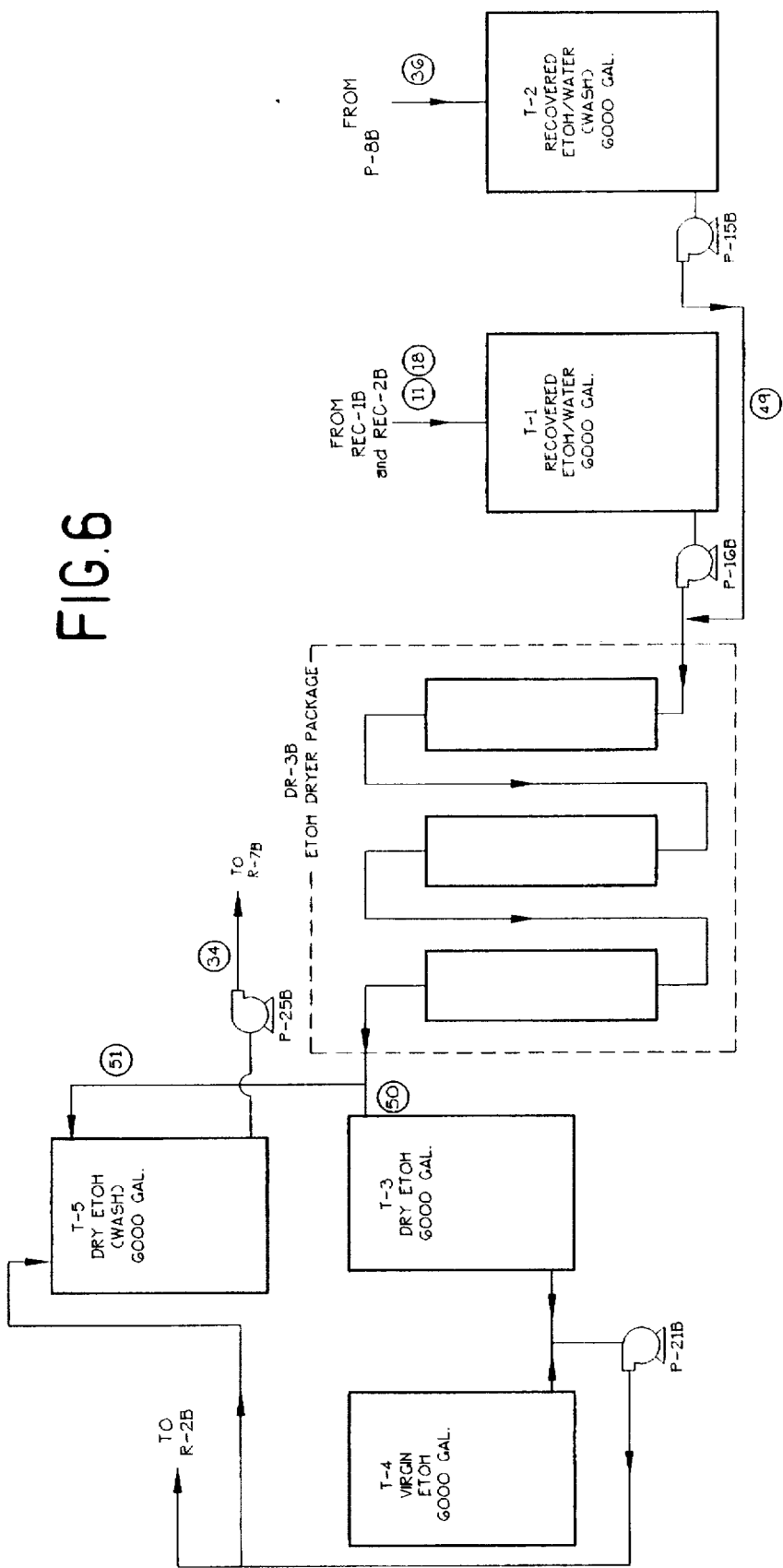
FIG. 6 is a process flow diagram showing the way the ethanol is recovered and reused.

As shown in FIG. 6, ethanol streams 11, 18, and 36 to be recovered enters tanks T-1 and T-2 from which it is sent by pumps P-15B and P-16B through a molecular sieve dryer DR-3B via a stream 49. The water is removed and sent to storage tanks. The water is recovered from the dryer DR-3B by steam heating of the molecular sieve containers.

Figure 7:
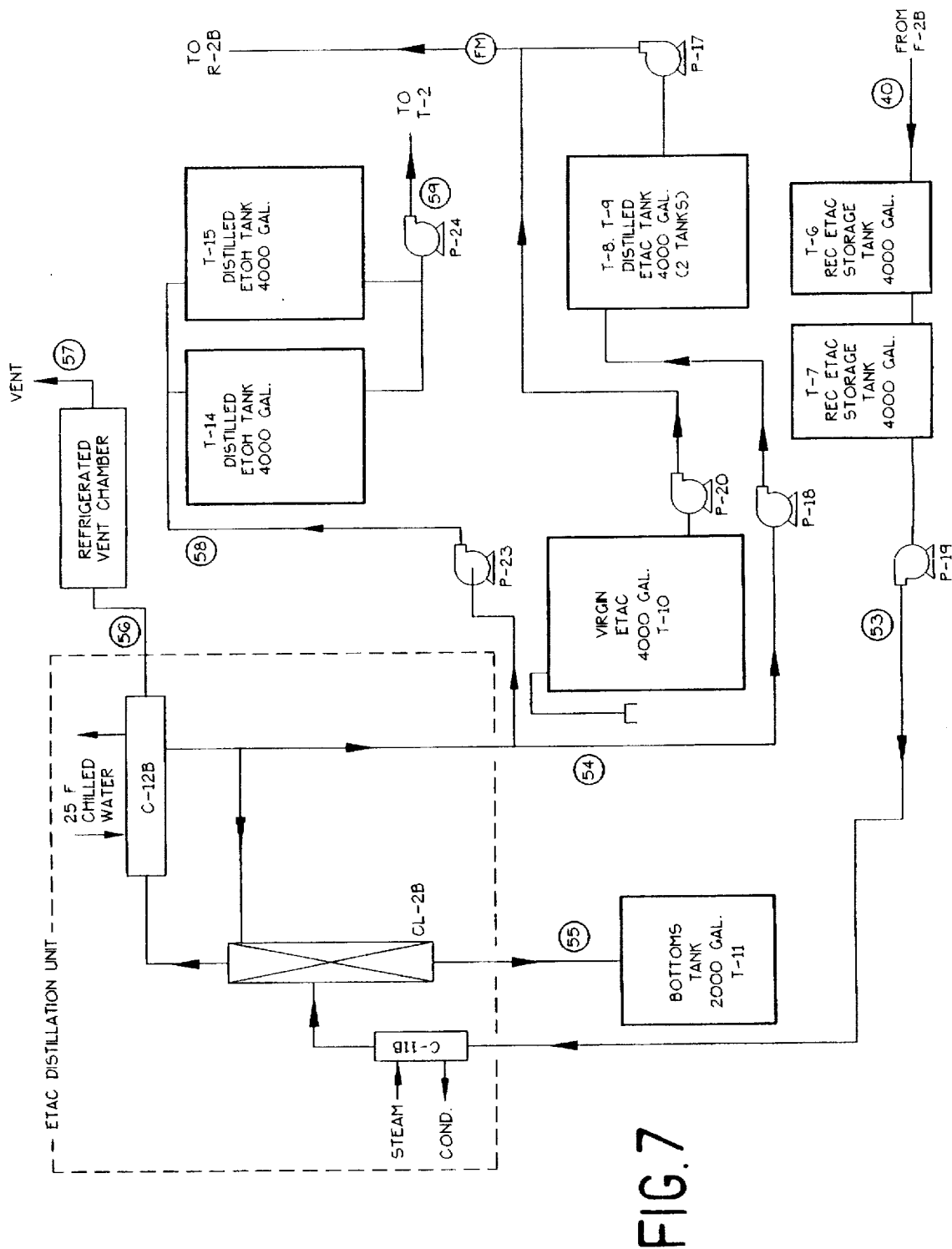
FIG. 7 is a process flow diagram showing the way the ethyl acetate is recovered and reused.

As shown in FIG. 7, the ethyl acetate stream 40 containing ethyl stearate and ethanol is recovered in tanks T-6 and T-7. It is sent by pump P-19 to a distillation column CL-2B via stream 53 from which the ethanol and ethyl acetate is removed. The removed ethyl acetate stream 54 is sent by pump P-18 to distilled ethyl acetate tanks T-8 or T-9. An ethanol stream 58, which comes off the distillation column CL-2B after the ethyl acetate stream 56, is sent by the pump P-23 to distilled ethanol tanks T-14 or T-15. The bottoms are removed via stream 55 and stored in tank T-11 They contain reusable ethyl stearate with ethanol that is not completely removed. This bottoms material can be combined with ethyl stearate and ethanol that is sent to tank R-1B (see FIG. 1) where the ethanol is mostly removed for use in subsequent esterifications. The recovered ethyl stearate reduces the amount of ethyl stearate which must be subsequently synthesized.

SUMMARY

The overall yield of sucrose stearate product, based on ethyl stearate, is approximately 65% by weight including all of the purification steps. Prior to purification, the reaction yield is 85–90%. This is excellent compared to previous processes where the reaction yield was only 70% by weight before any purification was achieved. Final yields, after purification, in those processes are estimated at about 50% by weight.

In the process of this invention, the liquid streams are recycled so that there is no liquid wastes. With the reuse of the water from the molasses evaporation, i.e., the condensate, this process may be called a "zero liquid discharge" process. The only effluent from the plant would be that water associated with the steam water, i.e., related to the operation of the boiler such as boiler "blow down" water, or water associated with cooling towers needed for the chillers. Extra precautions have also been used to minimize air emissions through extensive use of the refrigerated cold traps before the vacuum pumps and the condensers after the vacuum pumps.

The process of this invention, and virtually the same equipment utilized in connection with the production of sucrose stearate as depicted in FIGS. 1 through 7, can be used to make other esters. When the predominant chain length of the fatty acid is below C16, such as when making sucrose cocoate (predominantly sucrose laurate), some changes are necessary but the can be accommodated in the same facility. The equipment depicted in FIGS. 1 through 3 are operated in essentially the identical manner. The product purification of FIG. 4 is changed such that n-butanol and water is added to reactor R-7B instead of ethanol and water. Centrifuge F-1B is replaced by a liquid-liquid centrifuge which can be installed in parallel in a facility designed to produce both products. The aqueous stream is still sent via stream 32 to an evaporator (or by steam distillation) whereby the molasses are concentrated, the small amount of n-butanol in the water is recovered and some of the water. Stream 33 is a liquid stream in this case and it would be sent to an evaporation system to recover the ethanol which would be identical to the systems used for recovery of the DMSO (FIG. 3) or the ethanol (FIG. 2). The product (stream 37) with n-butanol removed is sent to vessel K-1B as a liquid and the remainder of the process is completed. In this case the product is still a liquid when it leaves the dryer and the thin film evaporator of FIG. 3 can be used to remove the ethyl acetate from the product. These products are frequently sold as a liquid in a mixture with ethanol and water.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention:

We claim:

1. A process for manufacturing a sugar ester product from a sugar and a fatty acid, comprising
   (a) reacting a fatty acid and methyl or ethyl alcohol in the presence of sulfuric acid catalyst to produce a fatty acid ester and water.
   (b) neutralizing the sulfuric acid catalyst with a metal carbonate to make a metal sulfate, and separating the fatty acid ester from the metal sulfate, the alcohol and the water.
   (c) reacting in the presence of a metal carbonate catalyst the fatty acid ester from step (b) with sugar dissolved in dimethyl sulfoxide to produce the sugar ester product and alcohol,
   (d) separating the dimethyl sulfoxide from the reaction mixture by vacuum distillation, and then adding water with the sugar ester product and unreacted fatty acid ester being emulsified and the unreacted sugar and the metal carbonate being dissolved in the water,
   (e) separating the emulsified sugar ester product and unreacted fatty acid ester from the water containing dissolved unreacted sugar and metal carbonate by breaking the emulsion of the sugar ester product and unreacted fatty acid ester,
   (f) purifying the sugar ester product from step (e) by dissolving the unreacted fatty acid ester in ethyl acetate to effect purification,
   (g) recovering substantially all the dimethyl sulfoxide, alcohol, and ethyl acetate for reuse in the process, and
   (h) recovering substantially all the unreacted sugar in a concentrated useful form.

2. The process of claim 1 where the reaction mixture of step (a) is monitored to detect completion of the reaction when no more than 1 percent by weight of the fatty acid remains in the reaction mixture.

3. The process of claim 1 where the reaction mixture of step (c) is monitored to detect completion of the reaction when no more than 15 percent by weight of the fatty ester remains in the reaction mixture.

4. The process of claim 1 where steps (a), (b), and (c) are by batch and the other steps are either batch or continuous.

5. The process of claim 1 where, upon completion of the reaction of step d, the metal carbonate catalyst is neutralized with sulfuric acid to make a metal sulfate, and in step (e) the water contains the dissolved metal sulfate.

6. The process of claim 1 where excess sugar is used in step (c) in order to favor the production of monoester product.

7. The process of claim 1 where the sugar is selected from the group consisting of sucrose, glucose, fructose, xylose, arabinose, lactose, melibiose, galactose, mannose, raffinose and cellobiose, and the fatty acid is derived from natural oils and fats.

8. The process of claim 7 where the fatty acid is selected from the group consisting of hexanoic, octanoic, decanoic, lauric, myristic, myristoletic, palmitic, stearic, oleic, ricinoleic, linoleic, linolenic, arachidic, eicosenoic, behenic, and erucic fatty acids.

9. The process of claim 1 where the reaction time and temperature in step (c) increases as the chain length of the fatty acid decreases.

10. The process of claim 9 where the reaction time is from 3 to 6 hours and the reaction temperature is from 90 to 105 degrees Celcius when the average carbon chain length of the fatty acid is 16 or greater, and the reaction time is from 8 to 24 hours and the reaction temperature is from 105 to 125 degrees Celcius when the average carbon chain length of the fatty acid is less than 16.

11. A process for manufacturing a sugar ester product from a sugar and a fatty acid, comprising
 (a) reacting a fatty acid and methyl or ethyl alcohol in the presence of sulfuric acid catalyst to produce a fatty acid ester and water, said fatty acid having an average carbon chain length less than 16
 (b) neutralizing the sulfuric acid catalyst with a metal carbonate to make a metal sulfate, and separating the fatty acid ester from the metal sulfate, the alcohol and the water,
 (c) reacting in the presence of a metal carbonate catalyst the fatty acid ester from step (b) with sugar dissolved in dimethyl sulfoxide to produce the sugar ester product and alcohol,
 (d) separating the dimethyl sulfoxide from the reaction mixture by vacuum distillation, and then adding water with the sugar ester product and unreacted fatty acid ester being emulsified and the unreacted sugar and the metal carbonate being dissolved in the water, and then dissolving the sugar ester product and unreacted fatty acid ester in a solvent which is immiscible with the water to thereby form two separate liquid phases, one phase including the solvent, the sugar ester product and unreacted fatty acid ester, and the other phase including the water, the unreacted sugar and the metal carbonate
 (e) separating the emulsified sugar ester product and unreacted fatty acid ester from the water containing dissolved unreacted sugar and metal carbonate by breaking the emulsion of the sugar ester product and unreacted fatty acid ester,
 (f) purifying the sugar ester product from step (e) by dissolving the unreacted fatty acid ester in ethyl acetate to effect purification,
 (g) recovering substantially all the dimethyl sulfoxide, alcohol, and ethyl acetate for reuse in the process, and
 (h) recovering substantially all the unreacted sugar in a concentrated useful form.

12. The process of claim 11 where the solvent is selected from the group consisting of n-butyl alcohol, 2-butanol, hexane, heptane, methyl isobutyl ketone, and isomers of amyl alcohol.

13. The process of claim 12 where the two phases are separated by filtration, decanting or centrifuging.

14. The process of claim 1 where for higher chain sugar ester where the average carbon chain length of the fatty acid is 16 or greater, step (e) comprises adding ethyl alcohol or methyl-ethyl ketone to the emulsion to break the emulsion of the sugar ester product and unreacted fatty acid ester.

15. The process of claim 14 where for an average carbon chain length of the fatty acid of 16 or greater, the mixture of of the sugar ester product and the unreacted fatty acid ester is washed between steps (e) and (f) with dry ethyl alcohol to remove water in the mixture.

16. The process of claim 1 where the metal carbonate is recovered from the water phase and used to neutralize the sulfuric acid in step (b).

17. The process of claim 1 where the sugar ester product and the unreacted fatty acid ester are recovered as mixture from step (e), and said mixture of the sugar ester product and the unreacted fatty acid ester is washed with a solvent for the unreacted fatty acid ester until the there is less than 5 percent by weight of the unreacted fatty acid ester remaining in the sugar ester product.

18. The process of claim 17 where the solvent is ethyl acetate, with the sugar ester product being finally purified by removal of traces of ethyl acetate so that no more than 350 part per million of ethyl acetate remain in the final sugar ester product.

19. The process of claim 1 where the yield in step (c) is from 85 to 90 percent.

20. The process of claim 1 where all liquid, solid, and solution streams from the process are reused or recovered.

21. The process of claim 1 where the metal carbonate is identical in both step (b) and (c).

22. The process of claim 1 where the dimethyl sulfoxide is refluxed during step (c) at a temperature above the boiling point of the alcohol to remove the alcohol produce during step (c).

23. The process of claim 1 where the separated dimethyl sulfoxide from step (d) is reused in the process.

24. The process of claim 1 the where separated alcohol and water from step (b) are reused in the process.

25. The process of claim 1 where excess alcohol is used in step (a) to drive the reaction essentially to completion, so that less than 1 percent by weight of the fatty acid remains.

26. The process of claim 1 employing an on-line method of monitoring and controlling said process comprising
 (a) measuring the concentration of process components in samples from the process using a spectrometric instrument to obtain spectral data characteristic of the process components,
 (b) analyzing the spectral data using a chi-squared mathematical technique to determine the unknown concentration of process components in said samples, and
 (c) monitoring the physical parameters of the process and altering said physical parameters based on the determination of concentration of process components in step (b) as required to optimize the process.

27. The process of claim 1 where the sugar used is sucrose and the sugar ester product comprises
 (a) at least 80% by weight mono-, di- and tri- esters,
 (b) less than 5% by weight free sucrose,
 (c) has an acid value is less than 6,
 (d) no more than 2% by weight ash,
 (e) no more than 350 parts per million ethyl acetate,
 (f) no more than 3 parts per million arsenic,
 (g) no more than 50 parts per million heavy metals,
 (h) no more than 10 parts per million lead,
 (i) no more than 10 parts per million methyl ethyl ketone,
 (j) no more than 10 parts per million methyl alcohol,
 (k) no more than 2 parts per million dimethyl sulfoxide,
 (l) no more than 10 parts per million isobutyl alcohol.

\* \* \* \* \*